United States Patent [19]

Halbert

[11] Patent Number: 4,637,880

[45] Date of Patent: Jan. 20, 1987

[54] APPARATUS AND METHOD FOR THERAPEUTIC IMMUNODEPLETION

[75] Inventor: Seymour P. Halbert, Miami, Fla.

[73] Assignee: Cordis Laboratories, Inc., Miami, Fla.

[21] Appl. No.: 616,789

[22] Filed: Jun. 1, 1984

Related U.S. Application Data

[63] Continuation of Ser. No. 326,134, Nov. 30, 1981, abandoned.

[51] Int. Cl.$^4$ ............................................. B01D 13/00
[52] U.S. Cl. .................................... 210/638; 210/264; 210/927
[58] Field of Search ................. 604/4, 5, 6; 210/264, 210/284, 323.2, 927, 638, 96.2

[56] References Cited

U.S. PATENT DOCUMENTS

| | | | |
|---|---|---|---|
| 3,638,794 | 2/1972 | Holzer | 210/264 X |
| 4,061,141 | 12/1977 | Hyden et al. | 128/214 R |
| 4,118,314 | 10/1978 | Yoshida | 210/638 |
| 4,127,481 | 11/1978 | Malchesky et al. | 210/321.1 X |
| 4,192,748 | 3/1980 | Hyden | 210/96.2 X |
| 4,201,673 | 5/1980 | Kanno et al. | 210/323.2 X |
| 4,228,013 | 10/1980 | Degenkolb et al. | 210/264 |
| 4,356,267 | 10/1982 | Callegaro et al. | 210/927 X |
| 4,375,414 | 3/1983 | Strahilevitz | 210/638 |

FOREIGN PATENT DOCUMENTS 5038141  3/1980  Japan ................................. 210/433.2

OTHER PUBLICATIONS

Terman et al., "Removal of Circulating Antigen and Immune Complexes with Immunoreactive Collodion Membranes", from FEBS Letters, vol. 68, No. 1, pp. 89-94, 9-1976, North-Holland Publishing Co.—Amsterdam.

*Primary Examiner*—Frank Spear

[57] ABSTRACT

A therapeutic apparatus for the removal of a harmful agent from blood is provided in the form of an array of hollow fiber bundles connected in parallel, wherein the interior surfaces of the individual hollow fibers are coated with a covalently bound proteinaceous or other immunoadsorbent selected for specific removal of the harmful agent. In the disclosed method the apparatus is optionally connected as an extracorporeal shunt between the artery and vein of a patient to be treated and the blood is alternately routed through one fiber bundle while the remaining fiber bundles undergo regeneration. Specific embodiments include the removal of rheumatoid factor by covalently bound immunoglobulin G and the removal of digoxin by covalently bound anti-digoxin.

7 Claims, 1 Drawing Figure

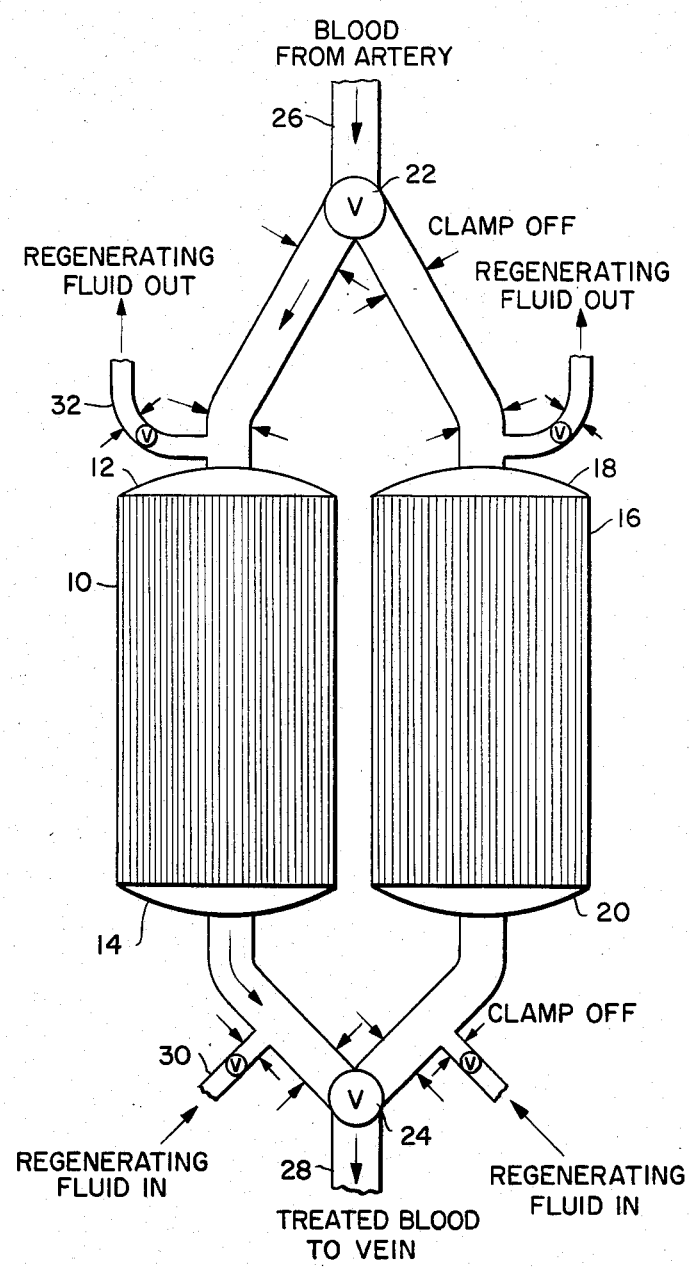

APPARATUS AND METHOD FOR THERAPEUTIC IMMUNODEPLETION

This is a continuation of Ser. No. 326,134, filed 11-30-81, now abandoned.

BACKGROUND OF THE INVENTION

Numerous illnesses are caused by excessive levels of harmful agents in the blood stream. Two large classes of such disturbances include those which are associated with:

(1) Substances in toxic excess concentrations, such as externally derived drugs, e.g. digoxin, gentamicin, etc. and internally derived substances, e.g. thyroxin in thyrotoxicosis, etc.; or (2) Abnormal auto-antibodies which are directed against normal tissue constituents, such as rheumatoid factor, anti-DNA, etc.

In some of these disturbances, particularly the latter group, recent studies have indicated that plasmapheresis exerts a beneficial therapeutic effect, apparently as a cleansing mechanism. However, plasmapheresis is a relatively crude method of removing unwanted deleterious substances, since it results in the depletion of virtually all plasma constituents, including many essential beneficial ones, in addition to the removal of the harmful agent. Ideally, a highly selective system is required which removes *only* the unwanted harmful agent, and leaves all the other plasma constituents unchanged in the patient. The resultant therapeutic effects would presumably be considerably more efficient and thorough, with no side effects due to the treatment.

Only one approach with the required high degree of selectivity is presently known. This approach involves immunological reagents (antibodies, antigens or haptens), which have been shown to possess remarkable degrees of specificity. The use of such reagents in solid phase has proven feasible in numerous demonstrations during the last 10 to 20 years. Thus, it has been established in the art that antibodies and antigens can be bound covalently to solid supports in a fully reactive state while retaining complete specificity. This "solid phase" technology is the basis for a large proportion of the sensitive radio-immunoassays and enzyme-immunoassays currently used in diagnostic laboratories.

The prior art literature reveals several suggested therapeutic methodologies employing solid-phase immunoadsorbent columns. Where the immunoadsorbent is adsorbed on a solid phase such as activated charcoal, there exists the possibility of leakage of the immunoadsorbent into the blood which might provoke an immune response within the patient, thus producing undesirable side effects. Even where such prior art columns have employed immunoadsorbents covalently bound to a particulate solid substrate, the column performance in the treatment of blood has proven to be less than entirely satisfactory, for use as a shunt between an artery and vein, because of the tendency of the packed column to become plugged. Another approach suggested in the literature is the use of an extracorporeal shunt in the form of a chamber containing a number of polymethylmethacrylate plates to which a proteinaceous immunoadsorbent is covalently bound. See: Holger Hyden "Enzyme Therapy and Immuno-adsorption by an Extra-Corporeal Device"; *Biomat.Med.Art.Org.*, 1980,8,(1), pp. 1-11. The limitations imposed by the use of such a device relate to the limited amount of surface area with bound immunoadsorbent and facility for regeneration.

Ideally, any extracorporeal shunt should be of a nature which allows therapeutic treatment to be conducted continuously over as long a period of time as is appropriate to the patient's condition. Accordingly, it is an object of the present invention to provide a therapeutic device having a solid phase immobilized immunoadsorbent specific for a harmful agent to be removed from blood, blood plasma or serum and of a nature which permits continuous, prolonged use as an extracorporeal shunt when connected between an artery and vein of a patient.

Consistent with the aforementioned objective, it is a further objective of the present invention to provide such a device which may be easily and rapidly regenerated without interruption of therapeutic treatment.

It is yet another object of the present invention to provide a relatively large surface area of bound immunoadsorbent relative to the volumetric flow rate of the blood undergoing treatment.

Yet another object of the invention is to provide such a device characterized by minimal pressure drop and susceptibility to plugging.

These and other objects and features of the present invention will become apparent to those skilled in the art from a reading of the description which follows in conjunction with the accompanying drawing.

SUMMARY OF THE INVENTION

This invention provides a hollow fiber therapeutic device for the removal of a harmful agent from blood, blood plasma or serum. The therapeutic device of the invention includes one or more hollow fiber bundles wherein the interior surface of each hollow fiber is coated with a proteinaceous or other immunoadsorbent covalently bonded to the hollow fiber solid phase. Preferably, a plurality of such hollow fiber bundles are employed in a parallel array so that a patient's blood may be continuously treated by passage through one or more selected bundles retaining immunoadsorbent capacity at a suitable level while other bundles, removed from service, are simultaneously undergoing regeneration. With such an array of parallel bundles the apparatus may be used as an extracorporeal shunt between an artery and a vein of a patient continuously, over any extended period of time suitable for treatment of the patient's condition. Specific examples of proteinaceous immunoadsorbents covalently bound to the fiber interiors in accordance with the present invention are human immunoglobulin G, for the treatment of rheumatoid arthritis and anti-digoxin for the removal of digoxin.

The method of this invention provides steps and means for continuous use over any predetermined period of time.

DESCRIPTION OF THE DRAWING

The sole drawing FIGURE is a schematic representation of an embodiment of the present invention including two hollow fiber bundles connected in parallel.

DESCRIPTION OF THE PREFERRED EMBODIMENTS

The hollow fiber bundles employed in the present invention are prepared from hollow fiber bundles of the type commercially available for use in an artificial kidney apparatus. Fiber bundles of this type are shown, for example, in U.S. Pat. No. 4,211,597 entitled "Method For Making Artificial Kidney" issued to Lipps et al and in U.S. Pat. No. 3,228,876 issued to Mahon, and are commercially available from the Cordis-Dow Corporation. The teachings of U.S. Pat. No. 4,211,597 and U.S. Pat. No. 3,228,876 are incorporated by reference herein. Such hollow fiber bundles contain thousands of small diameter hollow fibers typically composed of cellulose. The individual fibers are mounted within a common chamber wherein their open ends terminate in spaced, subdivided chambers or headers formed in each end of the main chamber. A proteinaceous or other immunoadsorbent specific to the harmful agent to be removed from a patient's blood is covalently bound to the interior cellulose fiber surfaces through a suitable coupling agent. The coupling agent may consist of aldehyde groups formed on the surface of the cellulose by treatment of the cellulose, for example, by sodium periodate. An alternative coupling technique is the introduction of reactive groups into the surface of the cellulose by treatment with a cyanagen bromide solution. In like manner, hollow fibers of polystyrene may be coated with a proteinaceous or other immunoadsorbent through isothiocyanate groups introduced onto the polystyrene surfaces in a manner taught by Halbert et al in U.S. Ser. No. 126,525, entitled "Insoluble Matrix and Reagent Coating For Use In Hepatitis Immunoassay." Yet another alternative is the use of hollow glass fibers having a proteinaceous immunoadsorbent covalently bound thereto through a silane coupling agent as taught, for example, in U.S. Pat. No. 3,652,761 issued to Weetall. Human immunoglobulin G and anti-digoxin and other specific immunoadsorbents may be covalently bound to the lumen surfaces of cellulose hollow fibers through the aforementioned coupling agents.

A hollow fiber bundle preferred for use in the present invention consists of a bundle of at least two hundred hollow cellulose fibers and, more preferably, up to ten thousand such fibers of the type disclosed in the aforementioned patents to Lipps et al and Mahon and further having the immunoadsorbent covalently bound to the fiber lumen surfaces through aldehyde or cyanogen bromide activated groups.

The drawing depicts an embodiment of the present invention wherein two hollow fiber bundles, generally designated 10 and 16, are connected in parallel for use as an extracorporeal shunt connected between an artery and vein of a patient to be treated for removal of some harmful agent from the bloodstream. The drawing shows an array of two fiber bundles, of the type described in U.S. Pat. No. 3,228,876 to Mahon, but having a specific immunoadsorbent covalently bound to the lumen surfaces. In actual use as an extracorporeal shunt inlet 26 is connected to an artery of the patient to be treated and outlet 28 is connected to a vein of the patient. Incoming blood from the artery is directed by valve 22, for example, to fiber bundle 10 and valve 24 is likewise positioned to direct the blood exiting fiber bundle 10 through outlet 28 to the patient's vein. The incoming blood enters header 12 wherein it is distributed for flow passage through the individual fibers of bundle 10, which preferably consist of approximately ten thousand parallel hollow cellulose fibers. Blood exiting bundle 10 is collected in header 14 and returned through valve 24 and outlet 28 to the patient's vein. Experimentation with the apparatus may establish a preferred service period for a single bundle and, at the expiration of such a period, the blood flow may be diverted from bundle 10 through valve 22 to header 18 through bundle 16 to be collected in header 20 and returned to the patient's vein through valve 24 and outlet 28. Alternatively, the treated blood may be sampled at 30 to determine when the blood flow should be diverted to the second bundle. After diversion of the blood flow to bundle 16, the blood contained in bundle 10 is thoroughly flushed out with a balanced salt solution. Then a low pH buffer, of approximately pH 3.0 or less, or another antigen-antibody dissociating solution is introduced at 30 through fiber bundle 10, exiting at 32. A preferred low pH buffer is 0.1 molar glycine hydrochloride of pH 2.5. After flushing with balanced salt solution, the unit is ready to be re-used. In this manner, the immunoadsorbent capacity of fiber bundle 10 is restored to its original value. In like manner, fiber bundle 16 may be regenerated after a predetermined period of time or detection of the immunoadsorbent capacity dropping to a predetermined level. An optional alternative to the valve depicted in the drawing is the use of surgical clamps at the points indicated by the double arrows (→←).

In the treatment of rheumatoid arthritis, the goal is the specific removal from the blood stream of the autoantibody (rheumatoid factor) which is considered to be involved in the pathogenesis of the disease. This autoantibody is specifically directed against a certain conformation of human immunoglobulin G (IgG) acting as antigen. This antigen may be isolated from human plasma and purified to a considerable degree. This "antigen", human IgG is covalently bound to the lumen surfaces of the aforementioned hollow fiber devices for use in the treatment of rheumatoid arthritis. After a predetermined period of time or after the immunoadsorption capacity of a given hollow fiber unit drops to a predetermined value, that hollow fiber unit is removed from service while the blood is diverted for circulation through an identical alternative unit. While the second unit is in service the first is regenerated for additional use. In the regeneration process, the bundle removed from service is first thoroughly rinsed with a sterile balanced salt solution to remove all the blood and plasma. Subsequently, the rinsed fiber bundle is washed with a buffer at a pH of approximately 2.5 to liberate the antibodies (rheumatoid factors) from their immunobond with the "antigen" (human IgG). After washing again with sterile balanced salt solution at neutral pH, the fully reactivated unit will once more be available for use in treating the patient's blood. Each unit is alternately used in this manner until the patient's plasma is essentially free of rheumatoid factor autoantibodies. In this manner, the unwanted harmful agent may be removed from the patient's blood without effecting any change on the other constituents of the blood.

Digoxin may be removed from a patient's blood in essentially the same manner as described above in conjunction with the treatment of rheumatoid arthritis. However, in the removal of digoxin the antibody against digoxin (anti-digoxin) is covalently bound to the lumen surfaces of the fiber bundles. The anti-digoxin may be prepared in goats and purified immunochemically.

In the systems described in the foregoing, arterial pressure is normally sufficient for circulating the blood through the hollow fiber units.

The invention may be embodied in other specific forms without departing from the spirit or essential characteristics thereof. For example, by choice of specific antigen or antibody covalently bound to the lumen surfaces of the hollow fibers, other units may be prepared for the treatment of various auto-immune disturbances such as systemic lupus erythematosus, myasthenia gravis, glomerulonephritis, auto-immune thyroiditis, etc. Each illness to be treated requires its own specific purified antigen or antibody immobilized in the solid phase, i.e. covalently bound to the lumen surfaces of the fibers. Likewise, similar systems may be used to reduce toxic levels of a wide variety of drugs, e.g. the antibiotic gentamicin, the anti-cancer agent methotrexate, the anti-asthmatic drug theophylline, the cardiac drugs, lidocaine and procainamide, drugs of abuse, heroin, etc. In these cases, the appropriate antibody would be covalently bound to the fiber lumen surfaces for each drug treatment. Thus, the embodiments described above should be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. Therapeutic extracorporeal shunt apparatus connectable to an artery and vein of a patient for removal of an agent from the patient's blood, said apparatus including provision for simultaneous treatment and on-line regeneration, comprising:
   (a) pick-up means for directing blood from an artery of the patient to the therapeutic extracorporeal shunt apparatus;
   (b) return means for directing blood to a vein of the patient from the therapeutic extracorporeal shunt apparatus;
   (c) a first blood flow path connecting said pick-up means and said return means and having closable ports for in-flow and out-flow of a regenerating fluid, comprising
      (i) a bundle of at least two hundred parallel hollow fibers having covalently bound to their inner surfaces an immunoadsorbent capable of binding said agent, thereby removing it from the patient's blood, and
      (ii) a header at each end of said bundle in fluid communication with the interior of the fibers in said bundle to provide a flow passage through the length of the interiors of said hollow fibers;
   (d) a second blood flow path, isolatable from said first blood flow path, connecting said pick-up means and said return means and having closable ports for in-flow and out-flow of a regenerating fluid, comprising
      (i) a bundle of at least two hundred parallel hollow fibers having covalently bound to their inner surfaces an immunoadsorbent capable of binding said agent, thereby removing it from the patient's blood, and
      (ii) a header at each end of said bundle in fluid communication with the interior of the fibers in said bundle to provide a flow passage through the length of the interiors of said hollow fibers;
   (e) first valve means for selectively flowing blood through said first blood flow path or said second blood flow path; and
   (f) second valve means for selectively flowing regenerating fluid through either said first blood flow path or said second blood flow path while blood is flowing through the other blood flow path,
wherein said parallel hollow fibers are of a number and size selected to provide for an extracorporeal blood volume and flow rate sufficient, under the impetus of arterial pressure, to provide adequate flow through and contact with the hollow fibers of said first blood flow path for efficacious, continuous treatment of said patient.

2. The therapeutic apparatus of claim 1 wherein said immunoadsorbent is an immunoglobulin.

3. The therapeutic apparatus of claim 1 wherein said immunoadsorbent is an antigen.

4. A continuous process for the removal of an agent from the blood of a patient comprising:
   (a) diverting blood from an artery of the patient to an extracorporeal shunt;
   (b) passing, under the impetus of arterial pressure, the blood so diverted through the hollow interiors of 200–10,000 parallel hollow fibers comprising a first hollow fiber bundle, until a predetermined operating point is reached;
   (c) removing said agent from the blood as it passes through said hollow fibers by means of an immunoadsorbent covalently bonded to the inner surfaces of said hollow fibers;
   (d) returning the blood exiting said hollow fiber bundle to a vein of the patient;
   (e) upon reaching said predetermined operating point, switching the flow of diverted blood to said vein through the hollow interiors of 200–10,000 parallel hollow fibers comprising a second hollow fiber bundle;
   (f) isolating said first hollow fiber bundle from the diverted blood flow;
   (g) passing a regenerating solution through said first hollow fiber bundle to regenerate the immunoadsorbent;
   (h) sequentially passing a wash solution through said first hollow fiber bundle to prepare it for restoration to service; and
   (i) switching the flow of diverted blood back to said first hollow fiber bundle.

5. A process in accordance with claim 4 wherein said immunoadsorbent is an immunoglobulin.

6. A process in accordance with claim 4 wherein said immunoadsorbent is an antigen.

7. A process in accordance with claim 4 wherein said regenerating solution is a low pH buffer.

* * * * *